(12) United States Patent
Clark et al.

(10) Patent No.: US 10,118,055 B2
(45) Date of Patent: Nov. 6, 2018

(54) TOPICAL ANTI-PRURITIC COMPOSITIONS AND METHODS OF ACTION OF SAME

(75) Inventors: Kathleen L. Clark, Medusa, NY (US); Joanne M. Fraser, Westerlo, NY (US)

(73) Assignee: STIEFEL LABORATORIES, INC., Coral Gables, FL (US)

( * ) Notice: Subject to any disclaimer, the term of this patent is extended or adjusted under 35 U.S.C. 154(b) by 797 days.

(21) Appl. No.: 13/155,965

(22) Filed: Jun. 8, 2011

(65) Prior Publication Data

US 2011/0237593 A1 Sep. 29, 2011

Related U.S. Application Data

(62) Division of application No. 11/190,050, filed on Jul. 27, 2005.

(51) Int. Cl.
| | |
|---|---|
| *A61K 31/5375* | (2006.01) |
| *A61K 31/137* | (2006.01) |
| *A61Q 17/00* | (2006.01) |
| *A61K 8/31* | (2006.01) |
| *A61K 8/37* | (2006.01) |
| *A61K 8/891* | (2006.01) |

(52) U.S. Cl.
CPC .............. *A61Q 17/00* (2013.01); *A61K 8/31* (2013.01); *A61K 8/37* (2013.01); *A61K 8/891* (2013.01); *A61K 31/5375* (2013.01); *A61K 2800/75* (2013.01)

(58) Field of Classification Search
CPC .......................... A61K 31/137; A61K 31/5375
USPC ........................................................ 514/537
See application file for complete search history.

(56) References Cited

U.S. PATENT DOCUMENTS

| | | | |
|---|---|---|---|
| 3,172,805 A * | 3/1965 | De Salva et al. .......... 514/239.2 |
| 4,389,418 A | 6/1983 | Burton | |
| 4,478,853 A | 10/1984 | Chaussee et al. | |
| 4,970,220 A | 11/1990 | Chaussee et al. | |
| 5,332,689 A | 7/1994 | Sandhu et al. | |
| 5,540,853 A | 6/1996 | Trinh et al. | |
| 5,576,346 A * | 11/1996 | Clemente et al. ............ 514/456 |
| 5,607,980 A | 3/1997 | McAtee et al. | |
| 5,665,364 A | 9/1997 | McAtee et al. | |
| 5,811,111 A | 9/1998 | McAfee et al. | |
| 5,811,114 A | 9/1998 | Knight et al. | |
| 5,833,999 A | 11/1998 | Trinh et al. | |
| 5,849,310 A | 12/1998 | Trinh et al. | |
| 5,939,427 A * | 8/1999 | Kagayama et al. .......... 514/291 |
| 5,961,997 A | 10/1999 | Swinehart | |
| 5,962,482 A | 10/1999 | Bissett et al. | |
| 5,976,556 A | 11/1999 | Norton et al. | |
| 6,086,903 A | 7/2000 | Trinh et al. | |
| 6,124,362 A | 9/2000 | Bradbury et al. | |
| 6,153,208 A | 11/2000 | McAfee et al. | |
| 6,183,766 B1 | 2/2001 | Sine et al. | |
| 6,190,678 B1 | 2/2001 | Hasenoehrl et al. | |
| 6,214,889 B1 | 4/2001 | Peterson et al. | |
| 6,217,889 B1 | 4/2001 | Lorenzi et al. | |
| 6,231,837 B1 | 5/2001 | Stroud et al. | |
| 6,267,975 B1 | 7/2001 | Smith, III et al. | |
| 6,294,186 B1 | 9/2001 | Beerse et al. | |
| 6,322,801 B1 | 11/2001 | Lorenzi et al. | |
| 6,423,329 B1 | 7/2002 | Sine et al. | |
| 6,428,799 B1 | 8/2002 | Cen et al. | |
| 6,451,777 B1 | 9/2002 | Bradbury et al. | |
| 6,491,933 B2 | 12/2002 | Lorenzi et al. | |
| 6,495,498 B2 | 12/2002 | Niemiec et al. | |
| 6,569,437 B1 | 5/2003 | Bishop et al. | |
| 6,599,513 B2 | 7/2003 | Deckers et al. | |
| 6,638,981 B2 | 10/2003 | Williams et al. | |
| 6,656,701 B2 | 12/2003 | Bishop et al. | |
| 6,656,928 B1 | 12/2003 | McCadden et al. | |
| 6,664,287 B2 | 12/2003 | Avery et al. | |
| 6,667,026 B1 | 12/2003 | Goldman et al. | |
| 6,762,158 B2 | 7/2004 | Lukenbach et al. | |
| 6,777,450 B1 | 8/2004 | George et al. | |
| 6,782,307 B2 | 8/2004 | Wilmott et al. | |
| 6,858,202 B2 | 2/2005 | Niemiec et al. | |
| 6,964,782 B1 | 11/2005 | Smith et al. | |
| 2002/0035046 A1 | 3/2002 | Lukenbach et al. | |
| 2002/0040056 A1 | 4/2002 | Ptchelintsev et al. | |
| 2004/0202706 A1 | 10/2004 | Koo et al. | |
| 2004/0258719 A1 * | 12/2004 | Takahashi ..................... 424/401 |
| 2005/0031547 A1 | 2/2005 | Tamarkin et al. | |
| 2005/0152993 A1 * | 7/2005 | De Oliveira .................. 424/669 |
| 2006/0004094 A1 | 1/2006 | Agisim et al. | |

OTHER PUBLICATIONS

Norman (Xerosis and pruritus in the elderly: recognition and management. Dermatol Ther. 2003;16(3):254-9).*
Yosipovitch et al. (Effect of topical pramoxine on experimentally induced pruritus in humans. J Am Acad Dermatol. Aug. 1997;37(2 Pt 1):278-80).*
Remington: The Science and Practice of Pharmacy's (p. 771 2006).*
Porter, K.T., "NACDS show offers treasure trove of new products", Drug Topics, Jul. 11, 2005.

* cited by examiner

*Primary Examiner* — Layla Soroush
(74) *Attorney, Agent, or Firm* — Nath, Goldberg & Meyer; Joshua B. Goldberg; Scott H. Blackman

(57) ABSTRACT

Topical anti-pruritic compositions and methods of using the same to treat pruritus. These anti-pruritic compositions are capable of temporarily or permanently reducing, inhibiting, treating, ameliorating, and/or preventing pruritic skin conditions, as well as other related skin conditions. In a particular aspect, the present formulations provide a quicker and more effective treatment of pruritus than do certain present pruritus-treating compositions.

8 Claims, No Drawings

TOPICAL ANTI-PRURITIC COMPOSITIONS AND METHODS OF ACTION OF SAME

This is a Divisional Application of U.S. patent application Ser. No. 11/190,050, filed on Jul. 27, 2005, the content of which is hereby incorporated by reference in its entirety.

FIELD OF THE INVENTION

The present subject matter relates generally to topical anti-pruritic compositions and to methods of using the same to treat pruritus. These anti-pruritic compositions are capable of temporarily or permanently reducing, inhibiting, treating, ameliorating, and/or preventing pruritic skin conditions, as well as other related skin conditions. In a particular aspect, the present formulations provide a quicker and more effective treatment of pruritus than do certain present pruritus-treating compositions.

BACKGROUND OF THE INVENTION

Pruritus is a dermatological disorder that is characterized by an unpleasant, itchy sensation of the skin. Typically pruritus provokes scratching, which is sometimes severe enough to irritate and inflame the skin of afflicted patients, and can lead to infection. Unfortunately, pruritus afflicts a large population with the elderly being especially vulnerable to moderate to severe outbreaks of pruritus.

Pruritus is most commonly caused by other dermatological conditions such as dry skin, xerosis, atopic dermatitis, allergic contact dermatitis, bullous pemphigoid, dermatitis herpetiformis, seborrheic dermatitis, folliculitis, psoriasis, lichen planus, mycosis fungoides, sunburn, local infection, scabies, and pediculosis corporis. However, pruritus can also be a side effect from another systemic irregularity or disease, such as iron deficiency anemia, severe chronic renal failure, neurodermatitis, delusions of parasitosis, polycythemia rubra vera, Hodgkin's lymphoma, malignant carcinoid, multiple myeloma, scleroderma, rapid weight loss (e.g. anorexia nervosa), hyperthyroidism (e.g. Grave's disease), urticaria, cholestasis, systemic infection, HIV, filariasis, schistosomiasis, onchocerciasis, ascariasis, hookworm, trichinosis, and parvovirus B19.

Patients suffering from pruritus induced by another dermatological disorder can further exacerbate the condition of the disorder by excessively scratching the affected area in an attempt to alleviate the pruritus. Many times this leads to patients inadvertently spreading the dermatological disorder to uninfected areas unintentionally, and with only minimal relief of the pruritus.

Likewise, patients suffering from pruritus induced by a systemic irregularity condition can possibly worsen the condition by excessively scratching the affected area. Even more of a concern is that a patient suffering from systemic induced pruritus will excessively scratch the affected area so much that the excessive scratching will lead to irritation and possibly infection.

Previous treatments for patients suffering from pruritus required administering a topical steroid, such as a topical corticosteroid, stabilized in a cream or ointment to the affected area of the patient. The most common corticosteroid used in this regard is hydrocortisone. However, as with all steroidal treatments, topical corticosteroids cause undesirable side effects in the patients being treated. Typical side effects experienced by patients being treated with topical corticosteroids include burning, itching, irritation, dryness, infection, striae, telangiectasia, dark red spots, painful pus-filled blisters in hair follicles, thinning of the skin, and easy bruising and tearing of the skin on the areas being treated. These side effects can exasperate the pruritus experienced by the patient, and can lead the patient to continue scratching the affected area.

Besides exasperating the pruritus, continued scratching by the patient as a result of these unwanted side effects can further inflame other dermatological skin conditions being experienced by the patient, as well as lead to additional inflammation and possible infection of the affected area. Additionally, some patients experiencing pruritus cannot take topical corticosteroid treatments due to allergic reactions from the treatment.

Moreover, patients being treated with topical corticosteroids need to be monitored by physicians to ensure that heavy absorption of corticosteroids through the skin does not lead to adrenal gland suppression, excessive fluid retention, lethargy, raised blood pressure, and diabetes.

Traditionally, previous topical corticosteroid treatments for pruritus are stabilized in heavy creams or ointments that leave a greasy feeling on the skin after applied. Typical previous pruritic creams and ointments contain a high level of lipophilic agents such as fatty acids, fatty acid esters, fatty alcohols, mineral oil, and petrolatum. High levels of lipophilic agents are used to help stabilize the topical corticosteroid, which can degenerate rapidly in an unstable composition.

However, these lipophilic agents used to stabilize the corticosteroid can reduce the topical availability and efficiency of the topical corticosteroid by smothering the corticosteroid in a lipid covering, or envelope. This is especially true of previously known compositions, which contain high levels of lipophilic agents.

For example, U.S. Pat. No. 4,797,402 to Dorsey discloses a hydrophilic ointment comprising hydrocortisone, peppermint oil, urea, surfactant, solvent, and white petrolatum used for treating skin disorders such as eczema, dermatitis, rashes, cutaneous candidiasis, pruritus ani, pruritus vulvae, and lichen simplex chronicus. Dorsey discloses using an amount of petrolatum in the ointment base from 64.45% to 93.79% by weight.

Similarly, U.S. Pat. No. 5,061,700 to Dow, et al. discloses topical ointments comprising glyceryl acetate, an oleaginous material, and a corticosteroid to treat skin disorders. In particular, Dow, et al. discloses the oleaginous material can be from 30% to 99.75% by weight.

Thus, the lipophilic agent not only makes the previous compositions heavy and greasy, but also reduces the topical availability of the corticosteroid in the topical compositions, as well as reduces the efficiency of the composition.

Accordingly, topical anti-pruritic compositions for treating pruritus in a patient that provide a more effective treatment of pruritus in comparison to treatment of pruritus achieved by administration of a topical composition containing a corticosteroid were previously unknown in the art. Moreover, many of the previously known treatments for pruritus were creams or ointments comprising high levels of lipophilic agents, which retard the topical availability and efficiency of the topical corticosteroid. Thus, a topical anti-pruritic composition comprising a low amount of lipophilic agents, while maintaining the stability of the anti-pruritic agent and increasing the efficiency and topical availability of the anti-pruritic agent was previously unknown in the art.

For these reasons, there remains a need in the art for topical anti-pruritic compositions that are more effective in treating pruritus in comparison to previous treatments containing a corticosteroid. In this regard, there remains a particular need for topical compositions that treat pruritus quicker than do hydrocortisone-containing compositions. Additionally, there remains a need in the art for a topical anti-pruritic composition comprising a low amount of lipophilic agents, while maintaining the stability of the anti-pruritic agent and increasing the efficiency and topical availability of the anti-pruritic agent. The present subject matter addresses these needs.

SUMMARY OF THE INVENTION

The present subject matter relates generally to topical anti-pruritic compositions.

In this regard, a preferred embodiment of the present subject matter relates to a method for treating pruritus in a patient comprising administering to a patient suffering from pruritus a first topical composition comprising at least one anti-pruritic agent and at least one occlusive skin conditioning agent, wherein the administration of the first composition provides a more effective treatment of the pruritus in comparison to treatment of pruritus achieved by administration of a second topical composition comprising a corticosteroid.

Another preferred embodiment of the present subject matter relates to a method for treating pruritus in a patient comprising administering to a patient suffering from pruritus a first topical composition comprising at least one anti-pruritic agent and at least one emollient, wherein the administration of the first composition provides a more effective treatment of the pruritus in comparison to treatment of pruritus achieved by administration of a second topical composition comprising a corticosteroid.

Yet another preferred embodiment of the present subject matter relates to a method of treating a patient suffering from pruritus comprising administering to a patient in need thereof a topical anti-pruritic composition comprising:
  (i) a therapeutically effective amount of an anti-pruritic agent;
  (ii) about 1 to about 10 percent by weight of an occlusive skin conditioning agent;
  (iii) about 0.5 to about 5 percent by weight of an organosiloxane; and
  (iv) an aqueous solvent,
wherein the topical anti-pruritic composition begins reducing symptoms of pruritus exhibited by the patient within about 30 minutes.

Moreover, another preferred embodiment of the present subject matter relates to a topical anti-pruritic composition comprising:
  (i) a therapeutically effective amount of an anti-pruritic agent;
  (ii) about 1 to about 10 percent by weight of an occlusive skin conditioning agent;
  (iii) about 0.5 to about 5 percent by weight of an organosiloxane; and
  (iv) an aqueous solvent.

DETAILED DESCRIPTION OF THE INVENTION

Definitions

As used herein, the terms "administering", "administration", and like terms refer to any method which, in sound medical or cosmetic practice, delivers the composition to a subject in such a manner as to provide a positive effect on a dermatological disorder, condition, or appearance. The compositions are preferably administered such that they cover the entire area to be treated. "Direct administration" refers to any method which, in sound medical or cosmetic practice, delivers the composition to a subject without the use of another composition, delivery agent, or device. "Indirect administration" refers to any method which, in sound medical or cosmetic practice, delivers the composition to a subject with the use of at least one other composition, delivery agent, or device.

As used herein, the phrases an "effective amount" or a "therapeutically effective amount" of an active agent or ingredient, or pharmaceutically active agent or ingredient, which are synonymous herein, refer to an amount of the pharmaceutically active agent sufficient enough to have a positive effect on the area of application. Accordingly, these amounts are sufficient to modify the skin disorder, condition, or appearance to be treated but low enough to avoid serious side effects, within the scope of sound medical or dermatological advice. A therapeutically effective amount of the pharmaceutically active agent will cause a substantial relief of symptoms when applied repeatedly over time. Effective amounts of the pharmaceutically active agent will vary with the particular condition or conditions being treated, the severity of the condition, the duration of the treatment, the specific components of the composition being used, and like factors.

As used herein, the phrase "occlusive skin conditioning agent" refers to an ingredient or ingredients that has the ability to retard the evaporation of water from the skin surface thereby increasing the water content of the skin.

As used herein, the phrase "pharmaceutically acceptable salts" refers to salts of certain ingredient(s) which possess the same activity as the unmodified compound(s) and which are neither biologically nor otherwise undesirable. A salt can be formed with, for example, organic or inorganic acids. Non-limiting examples of suitable acids include acetic acid, acetylsalicylic acid, adipic acid, alginic acid, ascorbic acid, aspartic acid, benzoic acid, benzenesulfonic acid, bisulfic acid, boric acid, butyric acid, camphoric acid, camphorsulfonic acid, carbonic acid, citric acid, cyclopentanepropionic acid, digluconic acid, dodecylsulfic acid, ethanesulfonic acid, formic acid, fumaric acid, glyceric acid, glycerophosphoric acid, glycine, glucoheptanoic acid, gluconic acid, glutamic acid, glutaric acid, glycolic acid, hemisulfic acid, heptanoic acid, hexanoic acid, hippuric acid, hydrobromic acid, hydrochloric acid, hydroiodic acid, hydroxyethanesulfonic acid, lactic acid, maleic acid, malic acid, malonic acid, mandelic acid, methanesulfonic acid, mucic acid, naphthylanesulfonic acid, naphthylic acid, nicotinic acid, nitrous acid, oxalic acid, pelargonic, phosphoric acid, propionic acid, saccharin, salicylic acid, sorbic acid, succinic acid, sulfuric acid, tartaric acid, thiocyanic acid, thioglycolic acid, thiosulfuric acid, tosylic acid, undecylenic acid, and naturally and synthetically derived amino acids.

If organic bases are used, poorly volatile bases are preferably employed, for example low molecular weight alkanolamines such as ethanolamine, diethanolamine, N-ethylethanolamine, N-methyldiethanolamine, triethanolamine, diethylaminoethanol, 2-amino-2-methyl-n-propanol, dimethylaminopropanol, 2-amino-2-methylpropanediol, and triisopropanolamine. Ethanolamine is particularly preferred in this regard. Further poorly volatile bases which may be mentioned are, for example, ethylenediamine, hexamethylenediamine, morpholine, piperidine, piperazine, cyclohexylamine, tributylamine, dodecylamine, N,N-dimethyldodecylamine, stearylamine, oleylamine, benzylamine, dibenzylamine, N-ethylbenzylamine, dimethylstearylamine, N-methylmorpholine, N-methylpiperazine, 4-methylcyclohexylamine, and N-hydroxyethylmorpholine.

Salts of quaternary ammonium hydroxides such as trimethylbenzylammonium hydroxide, tetramethylammonium hydroxide, or tetraethylammonium hydroxide can also be used, as can guanidine and its derivatives, in particular its alkylation products. However, it is also possible to employ as salt-forming agents, for example, low molecular weight alkylamines such as methylamine, ethylamine, or triethylamine. Suitable salts for the components to be employed according to the present subject matter are also those with inorganic cations, for example alkali metal salts, in particular sodium, potassium, or ammonium salts, alkaline earth metal salts such as, in particular, the magnesium or calcium salts, as well as salts with bi- or tetravalent cations, for example the zinc, aluminum, or zirconium salts. Also contemplated are salts with organic bases, such as dicyclohexylamine salts; methyl-D-glucamine; and salts with amino acids, such as arginine, lysine, and so forth. Also, the basic nitrogen-containing groups can be quaternized with such agents as lower alkyl halides, such as methyl, ethyl, propyl, and butyl chlorides, bromides, and iodides; dialkyl sulfates, such as dimethyl, diethyl, dibutyl, and diamyl sulfates; long chain halides, such as decyl, lauryl, myristyl, and stearyl chlorides, bromides, and iodides; asthma halides, such as benzyl and phenethyl bromides; and others. Water or oil-soluble or dispersible products are thereby obtained.

As used herein, the phrase "pruritic skin condition" refers to a condition in which at least one itchy sensation occurs on at least one skin area of a mammal.

As used herein, the phrase "therapeutic composition" refers to a composition which, upon administration, demonstrates a therapeutic affect upon a mammal.

Other terms as used herein are meant to be defined by their well-known meanings in the art.

Anti-Pruritic Skin Compositions

A preferred aspect of the subject matter expressed herein relates to various topical anti-pruritic compositions, and to methods for treating pruritus using the same. In particular, the present subject matter preferably relates to topical anti-pruritic compositions that provide a more effective treatment of pruritus in comparison to treatment of pruritus achieved by administration of another topical composition comprising a corticosteroid.

Topical compositions containing a corticosteroid have generally been used to temporarily alleviate and reduce pruritus in patients. However, as previously discussed, corticosteroids exhibit numerous unwanted side effects. In addition to this, some patients are allergic to topical corticosteroids. Accordingly, the presently preferred compositions are advantageous over previous corticosteroid-containing compositions in that they are more effective in treating patients suffering from pruritus and do not exhibit the unwanted side effects of the previously known compositions.

Additionally, the previously known compositions containing a corticosteroid also contained high amounts of lipophilic agents. However, these high amounts of lipophilic agents provided generally hydrophobic compositions that often feel greasy and heavy, and leave a long-lasting greasy residue on the skin after application. Additionally, the same high amounts of lipophilic agents that help stabilize the corticosteroid also stifled the topical availability and efficiency of the previously known compositions, rendering the previous compositions less effective.

In contrast, the presently preferred compositions contain lower levels of lipophilic agents in the form of an occlusive skin conditioning agent rather than as a composition base, thus making these compositions less greasy, heavy, and hydrophobic than the previous compositions, while maintaining the benefits of the lipophilic agents. Additionally, the presently preferred compositions are more efficient in treating pruritus since the anti-pruritic agent is more topically available, while also being remarkably stable.

In particular, the preferred topical anti-pruritic compositions are unique in that they are storage stable with respect to both the anti-pruritic agent, the lipophilic agent/occlusive skin conditioning agent, and the composition as a whole. Accordingly, these compositions have a decided advantage over previous anti-pruritic compositions containing a lipophilic agent as the formulation base in that they contain lower amounts of a lipophilic agent, while still limiting the amount of degradation experienced by the composition, resulting in a composition with improved long-term efficacy at temperatures of about 30° C. or below.

Further, the remarkable stability of the preferred compositions solves long felt difficulties in formulating anti-pruritic compositions having at least one lipophilic agent. Since these compositions are stable with much lower amounts of lipophilic agents, they provide unexpected advantages over the prior art compositions. For example, the lower amount of lipophilic agent still permits the presently preferred compositions to be manufactured in greater quantities without fear that the compositions produced will be wasted. Further, the presently preferred stable compositions with a lower amount of lipophilic agent as an occlusive skin conditioning agent provide the compositions with an enhanced effect in treating skin disorders treatable with an anti-pruritic agent and lipophilic agent over the previously known compositions.

In addition to utilizing lower amounts of lipophilic agents, which in turn increases the topical availability and efficiency of the anti-pruritic agent and anti-pruritic composition as a whole, the presently preferred compositions can contain an emollient to further increase the topical availability and efficiency of the anti-pruritic agent and anti-pruritic composition as a whole. By increasing the topical availability of the anti-pruritic agent, the presently preferred compositions have a greater efficiency in treating pruritus than previously known corticosteroid-containing compositions.

In a particularly preferred embodiment, the present compositions can comprise:
 (i) a therapeutically effective amount of an anti-pruritic agent;
 (ii) about 1 to about 10 percent by weight of an occlusive skin conditioning agent;
 (iii) about 0.5 to about 5 percent by weight of an organosiloxane; and
 (iv) an aqueous solvent.

Anti-Pruritic Agent

An essential component of the presently preferred compositions is at least one anti-pruritic agent or a derivative thereof. The anti-pruritic agent can provide minor to moderate pain relief, help alleviate itching, burning, and/or irritated sensations caused by pruritus and various other dermatological disorders, and help alleviate pruritus. The anti-pruritic agent is preferably present in the instant compositions in a therapeutically effective amount. In this regard, the present compositions preferably contain about 0.01% to about 20% by weight, and more preferably from about 0.1% to about 5% by weight, of the anti-pruritic agent.

Non-limiting examples of preferred anti-pruritic agents useful herein include pramoxine, diphenhydramine, benzocaine, lidocaine, bupivacaine, chloroprocaine, dibucaine, etidocaine, mepivacaine, tetracaine, dyclonine, hexylcaine, lignocaine, phenacaine, procaine, ketamine, phenol, butamben, butambenpicrate, cocaine, dimethisoquin, diperodon, dyclonine, methapyriline, oxyprocaine, p-buthylaminobenzoic acid 2-(die-ethylamino) ethyl ester, piperocaine, prilocaine, tripelennamine, dyclonine, resorcinol, cinchocaine, dexivacaine, diamocaine, levobupivacaine, oxethazaine, proparacaine, propoxycaine, pyrrocaine, risocaine, rodocaine, ropivacaine, pramocaine, proxazocain, 4-(3-(p-butoxyphenoxy)propyl) morpholine, gamma-morpholinopropyl 4-n-butoxyphenyl ether, p-butoxyphenyl gamma-morpholinopropyl ether, 4-[3-(4-butoxyphenoxy)-propyl] morpholine, menthol, camphor, menthyl anthranilate, and pharmaceutically acceptable salts thereof, derivatives, and mixtures thereof.

In a preferred aspect, the anti-pruritic agent can be any of pramoxine, pramocaine, proxazocin, 4-(3-(p-butoxyphenoxy) propyl) morpholine, gamma-morpholinopropyl 4-n-butoxyphenyl ether, p-butoxyphenyl gamma-morpholinopropyl ether, 4-[3-(4-butoxyphenoxy)-propyl]morpholine, a pharmaceutically acceptable salt thereof, a derivative thereof, or mixtures thereof. In a particularly preferred embodiment, the antipruritic agent is pramoxine or a pharmaceutically acceptable salt or derivative thereof.

Lipophilic Agents/Occlusive Skin Conditioning Agents

In preferred embodiments, the present compositions can additionally comprise at least one lipophilic agent as an occlusive skin conditioning agent. In this regard, the present compositions preferably contain about 1% to about 15% by weight, and more preferably from about 5% to about 10% of at least one lipophilic agent.

The lipophilic agent can help provide the softening, smoothing, lubricating, and skin conditioning features of the presently preferred compositions. Once applied to the skin, the occlusive skin conditioning agent can lower the transepidermal water loss (TEWL), or migration of moisture through the skin's tissues from deeper dermal tissues. Accordingly, by lubricating the skin, the occlusive skin conditioning agent of the presently preferred compositions can lower the amount of TEWL experienced, thus helping alleviate further dermatological disorders, such as pruritus. In this regard, the occlusive skin conditioning agent can help soften and lubricate the skin of patients suffering from pruritus, while the anti-pruritic agent helps alleviate the itchy sensations caused by the pruritus.

Preferred occlusive skin conditioning agents useful herein generally have low solubility in water, such that preferably less than about 10% by weight is soluble in water at 25° C., and more preferably less than about 1% by weight is soluble in water at 25° C. Additionally, the occlusive skin conditioning agents and/or emollients useful herein preferably can have a density of about 0.75 to about 1.65.

Preferred non-limiting examples of occlusive skin conditioning agents useful in the present compositions include petrolatum, red petrolatum, white petrolatum, liquid petrolatum, semi-solid petrolatum, light mineral oil, heavy mineral oil, white mineral oil, mineral oil alcohols, $C_7$-$C_{40}$ branched chain hydrocarbons, $C_{10}$-$C_{30}$ alcohol esters of $C_{10}$-$C_{30}$ carboxylic acids, $C_{10}$-$C_{30}$ alcohol esters of $C_{10}$-$C_{30}$ dicarboxylic acids, monoglycerides of $C_{10}$-$C_{30}$ carboxylic acids, diglycerides of $C_{10}$-$C_{30}$ carboxylic acids, triglycerides of $C_{10}$-$C_{30}$ carboxylic acids, ethylene glycol monoesters of $C_{10}$-$C_{30}$ carboxylic acids, ethylene glycol diesters of $C_{10}$-$C_{30}$ carboxylic acids, propylene glycol monoesters of $C_{10}$-$C_{30}$ carboxylic acids, propylene glycol diesters of $C_{10}$-$C_{30}$ carboxylic acids, $C_{10}$-$C_{30}$ carboxylic acid monesters and polyesters of sugars, vegetable oils, hydrogenated vegetable oils, olive oil, hydrogenated olive oil, Shea butter, polypropylene glycols, polypropylene glycol $C_4$-$C_{20}$ alkyl ethers, di $C_8$-$C_{30}$ alkyl ethers, synthetic hydrocarbons, calamine, derivatives thereof, and mixtures thereof.

In a particularly preferred embodiment, the occlusive skin conditioning agent is selected from the group consisting of petrolatum, red petrolatum, white petrolatum, liquid petrolatum, semi-solid petrolatum, light mineral oil, heavy mineral oil, white mineral oil, mineral oil alcohols, $C_7$-$C_{40}$ branched chain hydrocarbons, derivatives thereof, and mixtures thereof. In a most preferred embodiment, the occlusive skin conditioning agent is petrolatum.

Petrolatum, which is also known as petroleum jelly, and its derivatives are colloidal systems of nonstraight-chain solid hydrocarbons and high-boiling liquid hydrocarbons, in which most of the liquid hydrocarbons are held inside the micelles. See *The Merck Index*, Thirteenth Edition, Budavari et al., Eds., Merck & Co., Inc., Rahway, N.J. (2001); Schindler, *Drug. Cosmet. Ind.*, (1961); and the CTFA (Cosmetic, Toiletry, and Fragrance Association) *International Cosmetic Ingredient Dictionary and Handbook*, Tenth Edition (2004), which are incorporated by reference herein in their entirety.

In an alternative preferred embodiment, the occlusive skin conditioning agent is a straight or branched chain hydrocarbon having from about 7 to about 40 carbon atoms. Preferred, non-limiting examples of these hydrocarbon materials include dodecane, isododecane, squalane, cholesterol, hydrogenated polyisobutylene, docosane (i.e. a $C_{22}$ hydrocarbon), hexadecane, isohexadecane, derivatives thereof, and mixtures thereof. Also useful in this regard are the $C_7$-$C_{40}$ isoparaffins, which are $C_7$-$C_{40}$ branched hydrocarbons.

Additionally, further alternative occlusive skin conditioning agents useful in the present compositions include straight and branched chain hydrocarbons and aromatic derivatives of $C_{10}$-$C_{30}$ alcohol esters of $C_{10}$-$C_{30}$ carboxylic acids and of $C_{10}$-$C_{30}$ dicarboxylic acids, ethylene glycol monoesters of $C_{10}$-$C_{30}$ carboxylic acids, derivatives thereof, and mixtures thereof. Preferred carboxylic acids useful in this regard include $C_{10}$-$C_{30}$ straight chain, branched chain, and aryl carboxylic acids, as well as propoxylated and ethoxylated derivatives of these carboxylic acids. Additionally preferred, non-limiting examples of such alternative occlusive skin conditioning agents include ethylene glycol distearate, cetyl palmitate, myristyl myristate, stearyl stearate, cetyl stearate, behenyl behenate, caprylic/capric triglyceride, PEG-6 caprylic/capric triglyceride, PEG-8 caprylic/capric triglyceride, derivatives thereof, and mixtures thereof.

In addition to the occlusive skin conditioning agent, the present preferred compositions can optionally contain an additional lipophilic agent as an emollient. Many of the above-mentioned occlusive skin conditioning agents can alternatively be present in the instant compositions as an emollient in this regard. It would be readily apparent to a person of ordinary skill in the art exactly which of these components exhibit utility as an emollient.

Organosiloxane

The presently preferred compositions can further comprise at least one organosiloxane. Organosiloxanes useful in the present compositions can be volatile or nonvolatile, including but not limited to polyalkylsilicones, cyclic polyalkylsiloxanes, polydialkylsiloxanes, polydiarylsiloxanes, polyalkarylsiloxanes, or cyclomethicones having 1 to 9 silicon atoms.

Preferred polyalkylsiloxanes useful in this regard have a viscosity of from about 0.5 to about 100,000 centistokes at 25° C., and more preferably have a viscosity of less than 500 centistokes at 25° C., and correspond to the general chemical formula $R_3SiO[R_2SiO]_xSiR_3$ wherein $R_2$ and $R_3$ are alkyl groups, while x is an integer from about 0 to about 500. Non-limiting examples of preferred polyalkylsiloxanes useful in this regard include the Vicasil® series sold by General Electric Company and the Dow Corning® 200 series sold by Dow Corning Corporation.

Additionally, preferred cyclic polyalkylsiloxanes useful in the present compositions include those corresponding to the general chemical formula $[SiR_2O]_n$ wherein $R_2$ is an alkyl group and n is an integer from about 1 to about 9, more preferably n is an integer from about 3 to about 7, and most preferably n is an integer from about 4 to about 6. When $R_2$ is methyl, these materials are typically referred to as cyclomethicones. Preferred, non-limiting examples of such cyclomethicones include Dow Corning® 244 fluid, which primarily contains the cyclomethicone tetramer (i.e. n=4), Dow Corning® 344 fluid, which primarily contains the cyclomethicone pentamer (i.e. n=5), Dow Corning® 245 fluid, which primarily contains a mixture of the cyclomethicone tetramer and pentamer (i.e. n=4 and 5), Dow Corning® 345 fluid, which primarily contains a mixture of the cyclomethicone tetramer, pentamer, and hexamer (i.e. n=4, 5, and 6), derivatives thereof, and mixtures thereof.

In yet another alternative preferred embodiment, the organosiloxane can be a trimethylsiloxysilicate, which is a polymeric material corresponding to the general chemical formula $[(CH_2)_3]_x[SiO_2]_y$, wherein x is an integer from about 1 to about 500 and y is an integer from about 1 to about 500. A preferred, non-limiting example of a useful trimethylsiloxysilicate in this regard is Dow Corning® 593 fluid.

Other preferred organosiloxanes in this regard include dimethiconols, which are hydroxy terminated dimethyl silicones, represented by the general chemical formulas $R_5SiO[R_4SiO]_xSiR_4OH$ and $HOR_4SiO[R_4SiO]_xSiR_4OH$ wherein $R_4$ and $R_5$ are an alkyl group (preferably $R_4$ is methyl or ethyl, more preferably methyl) and x is an integer from 0 to about 500. Preferred, non-limiting examples of dimethiconols in this regard include mixtures with dimethicone or cyclomethicone, such as but not limited to, Dow Corning® 1401, 1402, and 1403 fluids.

In another alternative preferred embodiment, the organosiloxane is a polyalkylaryl siloxane, which includes polymethyphenyl siloxane, such as SF 1075 methylphenyl fluid sold by General Electric Company and 556 Cosmetic Grade phenyl trimethicone fluid sold by Dow Corning Corporation.

In a preferred embodiment, the organosiloxane used in the present compositions has a viscosity of less than about 500 centistokes. In a particularly preferred embodiment, the organosiloxane is dimethicone.

Aqueous Solvent

The present compositions additionally comprise an aqueous solvent. Preferably the aqueous solvent is present in the instant compositions from about 50% to about 95% by weight, and more preferably from about 60% to about 90% by weight.

Emollient

Certain of the presently preferred compositions can additionally comprise at least one emollient. Preferred emollients useful in this regard have the following structural formula:

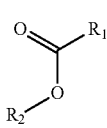

wherein $R_1$ can be a $C_7$-$C_{20}$ straight or branched alkane, $C_7$-$C_{20}$ straight or branched alkene, $C_7$-$C_{20}$ straight or branched alkyne, $C_7$-$C_{20}$ straight or branched alkanol, $C_7$-$C_{20}$ straight or branched alkenol, $C_7$-$C_{20}$ straight or branched alkynol, $C_7$-$C_{20}$ straight or branched ester, and $C_7$-$C_{20}$ straight or branched ether; and wherein $R_2$ can be a $C_1$-$C_8$ straight or branched alkane, $C_1$-$C_8$ straight or branched alkanol, $C_1$-$C_8$ straight or branched ether, $C_3$-$C_8$ cyclic hydrocarbon optionally substituted with at least one $R_3$, $C_3$-$C_8$ aromatic hydrocarbon optionally substituted with at lest one $R_3$, and $C_3$-$C_8$ aryl optionally substituted with at least one $R_3$;

wherein $R_3$ can be a $C_1$-$C_8$ straight or branched alkane, $C_1$-$C_8$ straight or branched alkene, $C_1$-$C_8$ straight or branched alkyne, $C_1$-$C_8$ straight or branched alkanol, $C_1$-$C_8$ straight or branched alkenol, $C_1$-$C_8$ straight or branched alkynol, $C_1$-$C_8$ straight or branched ester, and $C_1$-$C_8$ straight or branched ether.

Preferably, $R_1$ is a $C_{10}$-$C_{16}$ straight or branched alkane, $C_{10}$-$C_{16}$ straight or branched alkene, $C_{10}$-$C_{16}$ straight or branched alkyne, $C_{10}$-$C_{16}$ straight or branched alkanol, $C_{10}$-$C_{16}$ straight or branched alkenol, $C_{10}$-$C_{16}$ straight or branched alkynol, $C_{10}$-$C_{16}$ straight or branched ester, and $C_{10}$-$C_{16}$ straight or branched ether; and $R_2$ is a $C_1$-$C_8$ straight or branched alkane, $C_1$-$C_8$ straight or branched alkanol, and $C_1$-$C_8$ straight or branched ether.

More preferably, $R_1$ is a $C_{12}$-$C_{14}$ straight or branched alkane, $C_{12}$-$C_{14}$ straight or branched alkene, $C_{12}$-$C_{14}$ straight or branched alkyne, $C_{12}$-$C_{14}$ straight or branched alkanol, $C_{12}$-$C_{14}$ straight or branched alkenol, $C_{12}$-$C_{14}$ straight or branched alkynol, $C_{12}$-$C_{14}$ straight or branched ester, and $C_{12}$-$C_{14}$ straight or branched ether; and $R_2$ is a $C_2$-$C_5$ straight or branched alkane, $C_2$-$C_5$ straight or branched alkanol, and $C_2$-$C_5$ straight or branched ether.

The present compositions may contain about 0.01% to about 5% by weight, and more preferably from about 0.1% to about 1% by weight of an emollient.

Other ingredients commonly known to those of ordinary skill in the art as emollients are further contemplated for use in the present compositions.

Dermatologically Acceptable Excipients

The preferred compositions discussed herein can additionally comprise at least one dermatologically acceptable excipient commonly known to those of ordinary skill in the art as useful in topical compositions. Preferred, non-limiting examples of dermatologically acceptable excipients useful in these compositions are those selected from the group consisting of moisturizers, preservatives, gelling agents, colorants or pigments, antioxidants, radical scavengers, emulsifiers, pH modifiers, chelating agents, penetration enhancers, derivatives thereof, and mixtures thereof.

Moisturizers

The presently preferred compositions may optionally further contain at least one moisturizer. Preferably, the presently preferred compositions can comprise about 0.01% to about 10% by weight of at least one moisturizer. Preferred non-limiting examples of moisturizers that can optionally be included in these compositions include glycerin, pentylene glycol, butylene glycol, polyethylene glycol, sodium pyrrolidone carboxylate, alpha-hydroxy acids, beta-hydroxy acids, polyhydric alcohols, ethoxylated and propoxylated polyols, polyols, polysaccharides, panthenol, hexylene glycol, propylene glycol, dipropylene glycol, sorbitol, derivatives thereof, and mixtures thereof.

Preservatives

The presently preferred compositions may optionally further contain at least one preservative. Preferred non-limiting examples of preservatives that can optionally be included in these compositions include benzyl alcohol, methyl paraben, ethyl paraben, derivatives thereof, and mixtures thereof.

A particularly preferred preservative in this regard is benzyl alcohol or a derivative thereof. Additionally, the preservative is preferably present in an amount of about 0.1% to about 2.5% by weight of the overall weight of the composition.

Gelling Agents

The presently preferred compositions may optionally further contain a gelling agent. Preferred non-limiting examples of gelling agents that can optionally be included in these compositions include various cellulose agents, such as cellulosic polymers, methylcellulose, hydroxyethylcellulose, hydroxypropylcellulose, and hydroxypropylmethylcellulose. Additional, non-limiting examples of gelling agents include gum arabic, gum tragacanth, locust bean gum, guar gum, xanthan gum, cellulose gum, sodium carbomer, carbomer, polyacrylic polymers, derivatives thereof, and mixtures thereof. Other suitable gelling agents which may be useful in the present compositions include aqueous gelling agents, such as neutral, anionic, and cationic polymers, derivatives thereof, and mixtures thereof.

Exemplary polymers which may be useful in the preferred compositions in this regard include carboxy vinyl polymers, such as carboxypolymethylene. Additionally preferred gelling agents include Carbopol® and Carbomer® polymers (i.e. polyacrylic polymers) such as is available from Noveon Inc., Cleveland, Ohio.

The gelling agent is preferably present in the instant compositions in an amount of from about 0.01% to about 10%, more preferably from about 0.1% to about 5%, and most preferably from about 0.1% to about 2%, by weight.

Anti-Oxidants

The presently preferred compositions may optionally further contain at least one anti-oxidant. Preferably, the presently preferred compositions can comprise about 0.1% to about 5% by weight of at least one anti-oxidant. Preferred non-limiting examples of anti-oxidants that can optionally be included in these compositions include ascorbic acid, ascorbyl esters of fatty acids, magnesium ascorbyl phosphate, sodium ascorbyl phosphate, ascorbyl sorbate, tocopherol, tocopherol sorbate, tocopherol acetate, butylated hydroxy benzoic acid, thioglycolates, persulfate salts, 6-hydroxy-2,5,7,8-tetramethylchroman-2-carboxylic acid, lipoic acid, gallic acid, propyl gallate, uric acid, sorbic acid, lipoic acid, amines, N,N-diethylhydroxylamine, N-acetyl-L-cysteine, amino-guanidine, sulfhydryl compounds, glutathione, dihydroxy fumaric acid, lycine pidolate, arginine pilolate, nordihydroguaiaretic acid, bioflavonoids, curcumin, lysine, 1-methionine, proline, superoxide dismutase, silymarin, tea extracts, grape skin/seed extracts, melanin, rosemary extracts, derivatives thereof, and mixtures thereof.

Emulsifiers

The presently preferred compositions may optionally further contain an emulsifier. Preferably, the presently preferred compositions can comprise about 0.05% to about 15% by weight, and more preferably from about 0.5% to about 10% by weight of at least one emulsifier.

Preferred, non-limiting examples of specific emulsifiers useful in this regard include glycol esters, fatty acids, fatty alcohols, fatty acid glycol esters, fatty esters, fatty ethers, esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, polyethylene glycol 20 sorbitan monolaurate (polysorbate 20), polyethylene glycol 5 soya sterol, steareth-2, steareth-20, steareth-21, ceteareth-20, PPG-2 methyl glucose ether distearate, ceteth-10, polysorbate 80, cetyl phosphate, potassium cetyl phosphate, diethanolamine cetyl phosphate, polysorbate 60, glyceryl stearate, PEG-8 stearate, PEG-100 stearate, derivatives thereof, and mixtures thereof.

Any other emulsifiers known to those of skill in the art as useful in the formation of topical compositions are further contemplated herein.

pH Modifiers

The presently preferred compositions may optionally further contain a pH modifier. Preferably, the presently preferred compositions can comprise about 0.001% to about 1% by weight of a pH modifier. Preferred non-limiting examples of neutralizing pH modifiers that can optionally be included in these compositions include inorganic hydroxides, inorganic oxides, inorganic salts of weak acids, derivatives thereof, and mixtures thereof.

Preferred, non-limiting examples of inorganic hydroxides useful in this regard include ammonium hydroxide, alkali metal hydroxide, alkaline earth metal hydroxides, derivatives thereof, and mixtures thereof.

Preferred inorganic hydroxides useful in this regard include ammonium hydroxide, monovalent alkali metal hydroxides such as sodium hydroxide and potassium hydroxide, divalent alkali earth metal hydroxides such as calcium hydroxide and magnesium hydroxide, derivatives thereof, and mixtures thereof.

Preferred, non-limiting examples of inorganic oxides useful in this regard include magnesium oxide, calcium oxide, derivatives thereof, and mixtures thereof.

Preferred, non-limiting examples of inorganic salts of weak acids useful in this regard include ammonium phosphate (dibasic), alkali metal salts of weak acids such as sodium acetate, sodium borate, sodium metaborate, sodium carbonate, sodium bicarbonate, sodium phosphate (tribasic), sodium phosphate (dibasic), potassium carbonate, potassium bicarbonate, potassium citrate, potassium acetate, potassium phosphate (dibasic), potassium phosphate (tribasic), alkaline earth metal salts of weak acids such as magnesium phosphate and calcium phosphate, derivatives thereof, and mixtures thereof.

Chelating Agents

The presently preferred compositions may optionally further contain a chelating agent. Preferably, the presently preferred compositions can comprise about 0.01% to about 1% by weight of a chelating agent. Preferred non-limiting examples of chelating agents that can optionally be included in these compositions include citric acid, isopropyl (mono) citrate, stearyl citrate, lecithin citrate, gluconic acid, tartaric acid, oxalic acid, phosphoric acid, sodium tetrapyrophosphate, potassium monophosphate, sodium hexametaphosphate, calcium hexametaphosphate, sorbitol, glycine (aminoacetic acid), methyl glucamine, triethanolamine (trolamine), EDTA, DEG (dihydroxyethylglycine), DPTA (diethylene triamine pentaacetic acid), NTA (Nitrilotriacetic Acid), HEDTA (N-(hydroxyethyl)-ethylenetriaminetriacetic acid), aminocarboxylates, dimercaperol (BAL), larixinic acid (Maltol), unidentate ligands (fluoride and cyanide ions), diphenylthiocarbazone, 0-phenanthroline, barium diphenylamine sulfonate, sodium glucoheptonate, 8-hydroxyquinoline, olefin complexes (such as dicyclopentadienyl iron), porphyrins, phosphonates, pharmaceutically acceptable salts thereof, derivatives thereof, and mixtures thereof.

In addition to those enumerated above, any other pharmaceutically active anti-pruritic agent, occlusive skin conditioning agent, emollient, penetration enhancer, organosiloxane, moisturizer, preservative, gelling agent, colorant or pigment, antioxidant, radical scavenger, emulsifier, pH modifier, chelating agent, or other dermatologically acceptable excipient commonly known to those of ordinary skill in the art as useful in topical compositions is contemplated as useful in the compositions described herein. Further, any non-toxic, inert, and effective topical carrier may be used to formulate the compositions described herein. Well-known carriers used to formulate other topical therapeutic compositions for administration to humans will be useful in these compositions. Examples of these components that are well known to those of skill in the art are described in *The Merck Index*, Thirteenth Edition, Budavari et al., Eds., Merck & Co., Inc., Rahway, N.J. (2001); the CTFA (Cosmetic, Toiletry, and Fragrance Association) *International Cosmetic Ingredient Dictionary and Handbook*, Tenth Edition (2004); and the "Inactive Ingredient Guide", U.S. Food and Drug Administration (FDA) Center for Drug Evaluation and Research (CDER) Office of Management, the contents of which are hereby incorporated by reference in their entirety. Examples of such useful pharmaceutically acceptable excipients, carriers and diluents include distilled water, physiological saline, Ringer's solution, dextrose solution, Hank's solution, and DMSO, which are among those preferred for use herein.

These additional other inactive components, as well as effective formulations and administration procedures, are well known in the art and are described in standard textbooks, such as *Goodman and Gillman's: The Pharmacological Bases of Therapeutics,* 8th Ed., Gilman et al. Eds. Pergamon Press (1990) and *Remington's Pharmaceutical Sciences,* 17th Ed., Mack Publishing Co., Easton, Pa. (1990), both of which are incorporated by reference herein in their entirety.

In another particularly preferred embodiment, the presently preferred pharmaceutical compositions are formulated in a lotion, cream, ointment, gel, suspension, emulsion, foam, aerosol, or other pharmaceutically acceptable topical dosage form.

Methods of Treatment

Another preferred aspect of the present subject matter pertains to a method for treating pruritus in a patient comprising administering to a patient suffering from pruritus a topical composition as described herein, comprising at least one anti-pruritic agent, wherein the administration of this composition provides a more effective treatment of the pruritus in comparison to treatment of pruritus achieved by administration of another topical composition comprising a corticosteroid. The present methods are preferably carried out by administering a composition that contains, in addition to the anti-pruritic agent, at least one occlusive skin conditioning agent. In a particularly preferred embodiment, the present methods are carried out by administering a composition that comprises an anti-pruritic agent, an occlusive skin conditioning agent, an organosiloxane, and an aqueous solvent. In an alternative embodiment, the present methods are carried out by administering a composition that contains, in addition to the anti-pruritic agent, at least one emollient.

By way of non-limiting example, the present compositions provide this more effective treatment for patients suffering from pruritus and similar dermatological disorders by at least one of (i) providing topical compositions that are more efficient in treating pruritus by providing an anti-pruritic agent which is more topically available, (ii) providing topical compositions with reduced amounts of lipophilic agents thereby providing a lighter, less greasy, more hydrophilic composition, while still maintaining the benefits of having lipophilic agents present in the composition, (iii) providing topical compositions that have a quicker method of action in treating pruritus, (iv) providing compositions which reduce the incidence of pruritus in patients suffering from pruritus in substantially the same time, if not faster than previously known corticosteroid-containing compositions, and (v) providing compositions that are corticosteroid-free, thus eliminating the side effects experienced by administration of topical corticosteroids.

Speed of Action

In a particular preferred aspect, the presently preferred compositions exhibit a decreased amount of time needed to substantially treat a pruritic skin condition. In particular, the presently preferred compositions are substantially as effective, if not substantially more effective, in treating patients suffering from pruritus in substantially the same, or lesser amount of time than previously known topical corticosteroid composition. In fact, the presently preferred compositions require a shorter time period, upon application to a patient, to exhibit an appreciable reduction in pruritus than do many of the previously known corticosteroid-containing compositions.

This unexpected effectiveness of the presently preferred compositions may be due to the presence of at least one lipophilic agent as an occlusive skin conditioning agent, and thus in lower amounts than the previously known corticosteroid-containing compositions containing a lipophilic agent as a composition base. This, at least in part, can result in the higher topical availability of the anti-pruritic agent in comparison to that of previous corticosteroid compositions.

In this regard, the preferred compositions herein can preferably reduce the symptoms of pruritus exhibited by a patient within about 30 minutes, more preferably within about 15 minutes, and most preferably within about 2 minutes of their administration.

Additionally, the preferred compositions preferably can alleviate a pruritic skin condition of a patient, such that the patient no longer has moderate to severe itchy sensations on the affected area within about 4 hours, more preferably within about 1 hour, and most preferably within about 30 minutes.

Combination Therapy

In another preferred embodiment, the present preferred compositions may be used in combination with an additional pharmaceutical dosage form to enhance their effectiveness in treating a dermatological disease or disorder. In this regard, the present preferred compositions may be administered as part of a regimen additionally including any other pharmaceutical and/or pharmaceutical dosage form known in the art as effective for the treatment of a dermatological disorder. Similarly, a pharmaceutically active ingredient other than those specified herein can be added to the present preferred compositions to enhance their effectiveness in treating a dermatological disease or disorder. Accordingly, this additional pharmaceutically active ingredient or additional pharmaceutical dosage form can be applied to a patient either directly or indirectly, and concomitantly or sequentially, with the preferred compositions described herein.

In one embodiment in this regard, the present preferred composition and the additional pharmaceutical dosage form can be administered to a patient at the same time. In an alternative embodiment, one of the present preferred compositions and the additional pharmaceutical dosage form can be administered in the morning and the other can be administered in the evening.

Methods of Production

The present preferred compositions can be produced by various processes requiring various process steps. For example, one preferred process herein relates to a process for preparing a topical anti-pruritic composition described herein, said process comprising:
1) separately preparing an aqueous composition and an oily composition;
2) heating each of the aqueous and the oily compositions to a temperature of about 65-75° C.;
3) adding the oily composition to the aqueous composition at a temperature of about 65-75° C. to obtain an oil-in-water composition;
4) adding a therapeutically effective amount of an anti-pruritic agent to the oil-in-water composition;
5) cooling the oil-in-water composition to a temperature of about 35-45° C.; and
6) recovering a topical anti-pruritic composition.

In a preferred embodiment, the aqueous composition comprises water and a gelling agent. In another preferred embodiment, the oily phase comprises an occlusive skin conditioning agent, an organosiloxane, and optionally an emollient.

In a further preferred embodiment, the anti-pruritic agent is added to the oil-in-water composition after it has been dissolved in water. Additionally, a pH modifier or buffer can be added to the oil-in-water composition before the oil-in-water composition is cooled.

The present processes preferably form compositions comprising an emulsion having an oil phase and an aqueous phase. Non-limiting examples of specific types of emulsions that can be made according to this process include an oil-in-water emulsion, a water-in-oil emulsion, an oil-in-water-in-oil emulsion, and a water-in-oil-in-water emulsion. The formation of a specific type of emulsion will depend on the specific ingredients used in the process. In a preferred embodiment, the process will form compositions that are oil-in-water emulsions.

This particular preparation process is a non-limiting example of a possible process that can be used to prepare the preferred compositions. Other processes capable of preparing these compositions are further contemplated herein. Further, the individual phases of the preferred compositions (for example aqueous and oil phases) can be prepared sequentially in any order or concurrently; it is not necessary to prepare the oil phase before the aqueous phase is prepared in order to practice the present processes. Additionally, preferred compositions can be prepared according to either a batch process or continuously.

Further contemplated as within the scope of the present subject matter are pharmaceutical compositions produced according to the above-described process. If produced according to this process, these compositions exhibit chemical and physical stability suitable for topical administration.

The compositions produced according to these processes can be placed in a suitable containment vessel comprising a product contact surface composed of a material selected from the group consisting of glass, plastic, Teflon, polymeric structure, and mixtures thereof. These containment vessels are used to facilitate manufacturing, handling, processing, packaging, storage, and administration of said composition. Preferred containment vessels in this regard can be selected from the group consisting of plastic tubes and bottles.

Dosage

Appropriate dosage levels for the anti-pruritic agents contemplated in the preferred compositions and methods are well known to those of ordinary skill in the art and are selected to maximize the treatment of the previously described skin conditions. Dosage levels on the order of about 0.001 mg to about 5,000 mg per kilogram body weight of the occlusive skin conditioning agent and/or emollient and pharmaceutically active agent components are known to be useful in the treatment of the diseases, disorders, and conditions contemplated herein. Typically, this effective amount of the occlusive skin conditioning agent and/or emollient and pharmaceutically active agent will generally comprise from about 0.001 mg to about 100 mg per kilogram of patient body weight per day. Moreover, it will be understood that this dosage of ingredients can be administered in a single or multiple dosage units to provide the desired therapeutic effect.

If desired, other therapeutic agents can be employed in conjunction with those provided in the above-described compositions. The amount of pharmaceutically active ingredients that may be combined with the carrier materials to produce a single dosage form will vary depending upon the host treated, the nature of the disease, disorder, or condition, and the nature of the active ingredients.

The preferred pharmaceutical compositions may be given in a single or multiple doses daily. In a preferred embodiment, the pharmaceutical compositions are given from one to three times daily. Starting with a low dose twice daily and slowly working up to higher doses if needed is a preferred strategy. The amount of pharmaceutically active ingredients that may be combined with the carrier materials to produce a single dosage form will vary depending upon the host treated, the nature of the disease, disorder, or condition, and the nature of the active ingredients.

It is understood, however, that a specific dose level for any particular patient will vary depending upon a variety of factors, including the activity of the specific occlusive skin conditioning agent and/or emollient and pharmaceutically active agent; the age, body weight, general health, sex and diet of the patient; the time of administration; the rate of excretion; possible drug combinations; the severity of the particular condition being treated; and the form of administration. One of ordinary skill in the art would appreciate the variability of such factors and would be able to establish specific dose levels using no more than routine experimentation.

The optimal pharmaceutical formulations will be determined by one skilled in the art depending upon considerations such as the particular occlusive skin conditioning agent and/or emollient and pharmaceutically active agent combination and the desired dosage. See, for example, "Remington's Pharmaceutical Sciences", 18th ed. (1990, Mack Publishing Co., Easton, Pa. 18042), pp. 1435-1712, the disclosure of which is hereby incorporated by reference. Such formulations may influence the physical state, stability, rate of in vivo release, and rate of in vivo clearance of the essential lipids.

EXAMPLES

The following examples are illustrative of preferred compositions and are not intended to be limitations thereon. All polymer molecular weights are mean average molecular weights. All percentages are based on the percent by weight of the final delivery system or formulation prepared unless otherwise indicated and all totals equal 100% by weight.

Example 1

The following example illustrates the preparation of a present preferred lotion:

|  | % W/W |
|---|---|
| Pramoxine Hydrochloride | 1.08 |
| Benzyl Alcohol | 1.0 |
| Carbomer 940 | 0.7 |
| Cetyl Alcohol | 1.0 |
| Dimethicone | 0.9 |
| Glyceryl Stearate (&) PEG-100 Stearate | 0.51 |
| Isopropyl Myristate | 0.25 |
| Petrolatum | 5.0 |
| PEG 8 Stearate | 1.0 |
| Purified Water | 87.25 |
| Stearic Acid | 1.0 |
| Sodium Hydroxide | 0.308 |
|  | 100.0% |

Preparation of the Lotion:

An aqueous composition is prepared by heating 90% of the water to about 70° C. The Carbomer 940 is then hydrated in the aqueous composition with adequate stirring.

An oily composition is prepared by heating the cetyl alcohol, dimethicone, glyceryl stearate (&) PEG-100 stearate, isopropyl myristate, petrolatum, PEG 8 stearate, and stearic acid to about 70° C. and stirring until all the ingredients are melted.

The oily composition is then added to the aqueous composition at a temperature of about 70° C. to obtain an oil-in-water composition.

The pramoxine hydrochloride is then dissolved in a portion of the remaining water and added to the oil-in-water composition with mixing.

The sodium hydroxide is then dissolved in the remaining water and added to the oil-in-water composition with mixing.

The oil-in-water composition is then cooled to about 40° C. and the benzyl alcohol is added with mixing.

Example 2

A patient is suffering from pruritus. A preferred composition herein is topically administered to the patient. It would be expected that the patient would improve his/her condition or recover.

Example 3

A patient is suffering from a damaged skin lipid barrier induced by excessive scratching from a pruritic skin condition. A preferred composition herein is topically administered to the patient. It would be expected that the patient would improve his/her condition or recover.

Comparative Study

A randomized, single-blind, left/right, bilateral pilot study was carried out to compare the efficacy and safety of the present compositions to a 1% hydrocortisone cream. A study group of 30 subjects with mild atopic dermatitis were assigned each of two compositions. The first composition comprised the composition of Example 1, and the second composition comprised a 1% hydrocortisone cream. There was one application of each composition at baseline, with evaluations over 4 hours. All subjects applied study material in the office, with the first composition comprising the composition of Example 1 randomly applied to the right or left side of the body to a pruritic atopic area, and the second composition comprising the 1% hydrocortisone cream to the opposite side of the body in random order and staggered by 5 minutes.

Study subjects were primarily females (76.7%), with 56.7% of the subjects indicating they were Caucasian, 33.3% African American, and 10% selected Other, and a mean age of 32.3 years old. Study subjects were required to be at least 10 years of age, and to have a diagnosis or mild atopic dermatitis as determined by a 5 point grading scale for erythema, scaling, induration, and fissuring, as well as bilateral itching by the subject reporting at least a 50 on a Visual Analogue Scale (VAS). Subjects were asked to discontinue use of systemic corticosteroids for treatment of any condition before the study day. Subjects were also asked to discontinue the use of topical corticosteroids, non-steroidal immunosuppressants, and light treatments on week prior to the application of study materials.

The subjects were assessed using measurements for degree of pruritus at 2 minutes, 15 minutes, 30 minutes, 1 hour, 2 hours, 3 hours, and 4 hours after application. Itch sensations were determined by study subjects completing a 100 Millimeter VAS. A second, separate pruritus scale utilizing a scoring system of 1-10 was also completed for each side of the body at each time interval. Each subject also completed a Preference Questionnaire with 10 specific questions for each side of the body at 2 minutes and 4 hours.

All thirty subjects completed the study. However 2 study subjects were excluded from the VAS analysis since the site collected the baseline data for these subjects at the screening visit instead of on the day of the experiment. Similarly, 2 study subjects were excluded from the analysis of the pruritus scoring system for the same reasons.

The pruritus reduction relative to baseline for the first composition comprising the composition of Example 1 was significantly higher than that of the 1% hydrocortisone cream. Additionally, subject preference for the first composition comprising the composition of Example 1 was significant for at both the 2 minute and 4 hour measurement. 72% of subjects chose the composition of Example 1 at 2 minutes, and 74% of the subjects chose the composition of Example 1 at 4 hours.

Moreover, at 2 minutes, significantly more study subjects preferred the composition of Example 1 over the 1% hydrocortisone cream for "how well it is absorbed" and for "how it smells". At 4 hours, significantly more study subjects preferred the composition of Example 1 over the 1% hydrocortisone cream for "how well it is absorbed", "amount of dryness", and "amount of greasiness".

Below, Table 1 illustrates the VAS Pruritus Reduction from Baseline at Each Time Point for Composition 1 comprising the composition of Example 1 and 1% hydrocortisone cream.

TABLE 1

| Variable | N | Mean | Std. Dev. | Std. Error | t Value | Pr > \|t\| |
|---|---|---|---|---|---|---|
| Comp. 1*; 2 min. reduction | 26 | 12.85 | 24.88 | 4.88 | 2.63 | 0.0143 |
| Comp. 2**; 2 min. reduction | 25 | 6.2 | 19.28 | 3.86 | 1.61 | 0.1209 |
| Comp. 1*; 15 min. reduction | 28 | 16.11 | 25.52 | 4.82 | 3.34 | 0.0025 |
| Comp. 2**; 15 min. reduction | 27 | 13.63 | 20.3 | 3.91 | 3.49 | 0.0017 |
| Comp. 1*; 30 min. reduction | 28 | 22.68 | 30.66 | 5.8 | 3.91 | 0.0006 |
| Comp. 2**; 30 min. reduction | 27 | 26.22 | 20.43 | 3.93 | 6.67 | <0.0001 |
| Comp. 1*; 1 hour reduction | 28 | 27.43 | 30.59 | 5.78 | 4.74 | <0.0001 |
| Comp. 2**; 1 hour reduction | 27 | 32.7 | 23.07 | 4.44 | 7.37 | <0.0001 |
| Comp. 1*; 2 hour reduction | 28 | 30.57 | 32.94 | 6.22 | 4.91 | <0.0001 |
| Comp. 2**; 2 hour reduction | 27 | 31.81 | 23.9 | 4.6 | 6.92 | <0.0001 |
| Comp. 1*; 3 hour reduction | 28 | 36.43 | 29.01 | 5.48 | 6.64 | <0.0001 |
| Comp. 2**; 3 hour reduction | 27 | 38.74 | 24.25 | 4.67 | 8.3 | <0.0001 |
| Comp. 1*; 4 hour reduction | 28 | 34.43 | 36.95 | 6.98 | 4.93 | <0.0001 |
| Comp. 2**; 4 hour reduction | 27 | 36.52 | 21.61 | 4.16 | 8.78 | <0.0001 |

Below Table 2 illustrates the 1-10 scale pruritus reduction from baseline at each time point for composition comprising Example 1 and 1% hydrocortisone cream.

TABLE 2

| Variable | N | Mean | Std. Dev. | Std. Error | t Value | Pr > \|t\| |
|---|---|---|---|---|---|---|
| Comp. 1*; 2 min. reduction | 25 | 1.1 | 2.35 | 0.47 | 2.34 | 0.0282 |
| Comp. 2*; 2 min. reduction | 24 | 0.88 | 1.75 | 0.36 | 2.45 | 0.0225 |
| Comp. 1*; 15 min. reduction | 27 | 1.2 | 2.56 | 0.49 | 2.45 | 0.0216 |
| Comp. 2*; 15 min. reduction | 26 | 1.44 | 1.82 | 0.36 | 4.03 | 0.0005 |
| Comp. 1*; 30 min. reduction | 27 | 2.24 | 2.53 | 0.49 | 4.6 | <0.0001 |
| Comp. 2*; 30 min. reduction | 26 | 2.38 | 1.77 | 0.35 | 6.88 | <0.0001 |
| Comp. 1*; 1 hour reduction | 27 | 2.65 | 2.58 | 0.5 | 5.34 | <0.0001 |
| Comp. 2*; 1 hour reduction | 26 | 3.15 | 2.07 | 0.41 | 7.76 | <0.0001 |
| Comp. 1*; 2 hour reduction | 27 | 2.78 | 2.98 | 0.57 | 4.85 | <0.0001 |
| Comp. 2*; 2 hour reduction | 26 | 2.79 | 1.98 | 0.39 | 7.18 | <0.0001 |
| Comp. 1*; 3 hour reduction | 27 | 3.39 | 2.54 | 0.49 | 6.94 | <0.0001 |
| Comp. 2*; 3 hour reduction | 26 | 3.44 | 2.21 | 0.43 | 7.94 | <0.0001 |
| Comp. 1*; 4 hour reduction | 27 | 3.02 | 3.11 | 0.6 | 5.05 | <0.0001 |
| Comp. 2*; 4 hour reduction | 26 | 3.27 | 1.89 | 0.37 | 8.83 | <0.0001 |

*Comp. 1 comprises composition of Example 1
**Comp. 2 comprises 1% hydrocortisone cream Below Table 3 illustrates the VAS reduction differences at each time point for the composition comprising Example 1 and 1% hydrocortisone cream.

TABLE 3

| Variable | N | Mean | Std. Dev. | Std. Error | t Value | Pr > \|t\| |
|---|---|---|---|---|---|---|
| Reduction Difference 2 min. | 25 | 6.92 | 19.3 | 3.86 | 1.79 | 0.0856 |
| Reduction Difference 15 min. | 27 | 2.81 | 22.8 | 4.39 | 0.64 | 0.5267 |
| Reduction Difference 30 min. | 27 | −1.89 | 21.87 | 4.21 | −0.45 | 0.6573 |
| Reduction Difference 1 hour | 27 | −4.11 | 27.35 | 5.26 | −0.78 | 0.4418 |
| Reduction Difference 2 hours | 27 | 1.04 | 22.19 | 4.27 | 0.24 | 0.81 |
| Reduction Difference 3 hours | 27 | −1.15 | 22.39 | 4.31 | −0.27 | 0.792 |
| Reduction Difference 4 hours | 27 | −0.19 | 27.85 | 5.36 | −0.03 | 0.9727 |

Below Table 4 illustrates the 1-10 scale reduction differences at each time point for the composition comprising Example 1 minus the 1% hydrocortisone cream.

TABLE 4

| Variable | N | Mean | Std. Dev. | Std. Error | t Value | Pr > \|t\| |
|---|---|---|---|---|---|---|
| Reduction Difference 2 min. | 24 | 0.27 | 1.87 | 0.38 | 0.71 | 0.4853 |
| Reduction Difference 15 min. | 26 | −0.15 | 2.34 | 0.46 | −0.33 | 0.7407 |
| Reduction Difference 30 min. | 26 | −0.06 | 1.78 | 0.35 | −0.17 | 0.87 |
| Reduction Difference 1 hour | 26 | −0.4 | 2.52 | 0.49 | −0.82 | 0.4219 |
| Reduction Difference 2 hours | 26 | 0.17 | 1.98 | 0.39 | 0.44 | 0.6604 |
| Reduction Difference 3 hours | 26 | 0.08 | 2.02 | 0.4 | 0.19 | 0.8475 |
| Reduction Difference 4 hours | 26 | −0.1 | 2.51 | 0.49 | −0.2 | 0.8465 |

Overall, this study suggests that the use of the composition of Example 1 is an effective regimen for treatment of pruritus, and is substantially just as effective as this 1% hydrocortisone treatment. In particular, the present compositions appear to have a significantly higher speed of action than the 1% hydrocortisone treatment. Such hydrocortisone-based treatments are presently considered by some to be the treatment of choice for pruritus. These results are unexpected given the current standard of care using corticosteroids.

Accordingly, it would further be expected that the use of the composition of Example 1 has a significantly higher speed of action than topical hydrocortisone treatments comprising about 0.5% to about 2% of hydrocortisone for the treatment of pruritus. In particular, it would be expected that the present compositions have a significantly higher speed of action than topical hydrocortisone treatments comprising about 0.75% to about 1% of hydrocortisone for the treatment of pruritus.

Additionally, it would be expected that the results herein described would be similarly observed for any period of treatment or treatment regimen useful for treating pruritus. This includes daily administration of the compositions during the period of treatment, one or more daily administration of the topical compositions, or intermittent administration of the topical compositions. Further, the period of treatment contemplated herein can be any sufficient period of time to observe a reduced incidence of the pruritus, for example from about 2 minutes to about 4 hours, but in most cases more than 30 minutes, minimum.

Intermittent administration contemplated herein includes administration conducted other than daily administration. Such intermittent administration is typically conducted when a patient commences a new treatment, as a treatment is in its final stages (i.e. as the patient is weaned off of the treatment), or as part of a maintenance regimen. Typically, intermittent administration is conducted more than once per week, but less than once per day. This intermittent treatment is especially useful when a patient starts a new treatment regimen to build their tolerance to the new medicine, and is typically followed by a more regular administration regimen.

Accordingly, further contemplated herein is the intermittent administration of the topical composition after said period has ended to maintain the reduced incidence of pruritus.

The present subject matter being thus described, it will be apparent that the same may be modified or varied in many ways. Such modifications and variations are not to be regarded as a departure from the spirit and scope of the present subject matter, and all such modifications and variations are intended to be included within the scope of the following claims.

We claim:

1. A method for treating pruritus in a patient comprising administering to a patient suffering from pruritus a first topical composition that is a lotion consisting essentially of pramoxine or a pharmaceutically acceptable salt thereof in an amount from about 0.1 to about 5% by weight,
at least one occlusive skin conditioning agent in an amount from about 1 to about 10% by weight,
an organosiloxane in an amount from about 0.5 to about 5% by weight,
an emulsifier in an amount from about 0.5 to about 10% by weight,
a gelling agent selected from the group consisting of gum arabic, gum tragacanth, locust beam gum, guar gum, xanthan gum, and carbomer, in an amount of about 0.1 to about 2% by weight,
an emollient in an amount of about 0.01 to about 5% by weight,
and an aqueous solvent in an amount from about 60 to about 90% by weight, wherein the administration of said first composition provides a more effective treatment of said pruritus in comparison to treatment of pruritus achieved by administration of a second topical composition comprising about 1% by weight hydrocortisone.

2. The method of claim 1, wherein said occlusive skin conditioning agent is petrolatum.

3. The method of claim 1, wherein said emollient has the following structural formula:

wherein $R_1$ can be a $C_7$-$C_{20}$ straight or branched alkane, $C_7$-$C_{20}$ straight or branched alkene, $C_7$-$C_{20}$ straight or branched alkyne, $C_7$-$C_{20}$ straight or branched alkanol, $C_7$-$C_{20}$ straight or branched alkenol, $C_7$-$C_{20}$ straight or branched alkynol, $C_7$-$C_{20}$ straight or branched ester, and $C_7$-$C_{20}$ straight or branched ether; and wherein $R_2$ can be a $C_1$-$C_8$ straight or branched alkane, $C_1$-$C_8$ straight or branched alkanol, $C_1$-$C_8$ straight or branched ether, $C_3$-$C_8$ cyclic hydrocarbon optionally substituted with at least one $R_3$, $C_3$-$C_8$ aromatic hydrocarbon optionally substituted with at least one $R_3$, and $C_3$-$C_8$ aryl optionally substituted with at least one $R_3$;

wherein $R_3$ can be a $C_1$-$C_8$ straight or branched alkane, $C_1$-$C_8$ straight or branched alkene, $C_1$-$C_8$ straight or branched alkyne, $C_1$-$C_8$ straight or branched alkanol, $C_1$-$C_8$ straight or branched alkenol, $C_1$-$C_8$ straight or branched alkynol, $C_1$-$C_8$ straight or branched ester, and $C_1$-$C_8$ straight or branched ether.

4. The method of claim 1, wherein said topical antipruritic composition begins reducing symptoms of pruritus exhibited by said patient within about 15 minutes.

5. The method of claim 4, wherein said topical antipruritic composition begins reducing symptoms of pruritus exhibited by said patient within about 2 minutes.

6. The method of claim 1, wherein said topical antipruritic composition alleviates said pruritus within about 4 hours.

7. The method of claim 6, wherein said topical antipruritic composition alleviates said pruritus within about 1 hour.

8. The method of claim 3, wherein said emollient is isopropyl myristate.

* * * * *